United States Patent
Champseix et al.

(10) Patent No.: US 8,968,655 B2
(45) Date of Patent: Mar. 3, 2015

(54) APPARATUS FOR HANDLING TUBES, IN PARTICULAR AN AUTOMATIC BLOOD ANALYSIS APPARATUS

(75) Inventors: Serge Champseix, Tarnac (FR); Henri Champseix, Saint Gely du Fesc (FR); Laurent Damonneville, Castelnau le Lez (FR)

(73) Assignee: C2 Diagnostics, Montpellier (FR)

( * ) Notice: Subject to any disclaimer, the term of this patent is extended or adjusted under 35 U.S.C. 154(b) by 960 days.

(21) Appl. No.: 12/447,953

(22) PCT Filed: Oct. 16, 2007

(86) PCT No.: PCT/FR2007/001690
§ 371 (c)(1), (2), (4) Date: Apr. 30, 2009

(87) PCT Pub. No.: WO2008/056040
PCT Pub. Date: May 15, 2008

(65) Prior Publication Data
US 2010/0064826 A1   Mar. 18, 2010

(30) Foreign Application Priority Data

Oct. 30, 2006 (FR) ...................... 06 09520

(51) Int. Cl.
*G01N 21/00* (2006.01)
*B01L 3/00* (2006.01)
(Continued)

(52) U.S. Cl.
CPC ............ *G01N 35/04* (2013.01); *G01N 35/1079* (2013.01); *G01N 2035/00524* (2013.01)
USPC .................. 422/65; 422/62; 422/63; 422/66; 422/67; 422/430

(58) Field of Classification Search
CPC ................ G01N 35/1079; G01N 2035/00524; G01N 35/04; G01N 2035/041; G01N 2035/0412; G01N 2035/0425; G01N 35/1065; B01F 11/0017; B01F 11/0037; B01F 9/002; B01F 9/06
USPC ......... 422/430, 62, 63, 65–67, 501, 524–526, 422/300, 933, 554
See application file for complete search history.

(56) References Cited

U.S. PATENT DOCUMENTS 4,485,594 A * 12/1984 Guertin et al. .................... 451/5
4,518,264 A   5/1985 Nohso
(Continued)

FOREIGN PATENT DOCUMENTS

| FR | 2692358 | 12/1993 |
|---|---|---|
| FR | 2730315 | 8/1996 |
| FR | 2812088 | 1/2002 |

OTHER PUBLICATIONS

International Search Report dated Mar. 10, 2008 from corresp PCT/FR2007/001690.
(Continued)

*Primary Examiner* — Dean Kwak
(74) *Attorney, Agent, or Firm* — Young & Thompson (57) ABSTRACT

Apparatus (1) includes a device (20) for moving at least one compartment (2) in the apparatus, the compartment forming a support for tubes (3), which apparatus further includes elements (50) for taking a specimen of a product contained in the tubes, the movement device (20) including elements (21) for guiding the compartment during movement of the compartment and further including stirring members (27) for the guiding elements, the movement device being mounted on a chassis (4) of the apparatus.

21 Claims, 8 Drawing Sheets

(51) Int. Cl.
*G01N 35/04* (2006.01)
*G01N 35/10* (2006.01)
*G01N 35/00* (2006.01)

(56) References Cited

U.S. PATENT DOCUMENTS

| | | | |
|---|---|---|---|
| 4,609,017 A | 9/1986 | Coulter et al. | |
| 4,921,676 A | 5/1990 | Otani | |
| 5,158,895 A * | 10/1992 | Ashihara et al. | 436/526 |
| 5,250,440 A * | 10/1993 | Kelln et al. | 436/48 |
| 5,431,201 A * | 7/1995 | Torchia et al. | 141/98 |
| 5,578,268 A * | 11/1996 | Champseix et al. | 422/63 |
| 5,665,309 A | 9/1997 | Champseix et al. | |
| 6,818,182 B2 | 11/2004 | Le Comte et al. | |
| 7,220,385 B2 * | 5/2007 | Blecka et al. | 422/64 |
| 7,678,331 B2 * | 3/2010 | Shanafelter | 422/65 |
| 2002/0021983 A1 * | 2/2002 | Comte et al. | 422/65 |
| 2005/0196320 A1 * | 9/2005 | Veiner et al. | 422/63 |
| 2005/0226771 A1 * | 10/2005 | Lehto et al. | 422/63 |
| 2006/0013729 A1 * | 1/2006 | Carey et al. | 422/63 |

OTHER PUBLICATIONS

European Search Report dated Jun. 17, 2007 from corresp FR 0609520.

* cited by examiner

FIG_1

FIG_4

FIG_7

FIG_8

FIG_9

FIG_10

APPARATUS FOR HANDLING TUBES, IN PARTICULAR AN AUTOMATIC BLOOD ANALYSIS APPARATUS

BACKGROUND OF THE INVENTION

The present invention relates to devices for handling racks for tubes in an analysis apparatus, in particular an automatic blood analysis apparatus.

The present invention also relates to associated methods for moving said racks in the apparatus.

Hereafter reference will be made essentially to the analysis of blood samples. However, this must not be considered as limitative.

In view of the analysis, the samples, in particular the blood samples are generally contained in tubes. Each tube is hermetically sealed by a stopper which may be pierced. Taking a specimen from the tube is carried out through the stopper, using a sampling needle. For ease of handling, these tubes are arranged in racks. Each rack can for example contain 5 tubes arranged side by side, parallel and substantially in the same plane.

During the movement of a rack in the apparatus, the rack can be subjected to several handling operations. Generally, these handling operations are:
- the loading of the rack into the apparatus;
- the unloading of the rack, once analyses have been carried out;
- the movement of the rack in the apparatus, in particular between a loading position, an analysis position and an unloading position; and,
- the agitation of the contents of the tube, with a view to its homogenization. Such homogenization is particularly useful in the case of blood samples, in order to ensure that the sample specimen taken from a tube is truly representative of the contents of the tube.

Most automated haematology devices use horizontal loading devices. These devices are bulky, expensive and complex. They may moreover, due to their complexity, present problems of reliability. Such loading devices are described in the documents FR2692358 and FR2812088.

Other automatic devices use magnetic vertical loading. Such magnetic loading, in particular described in the document U.S. Pat. No. 4,609,017, requires a metal plate to be fixed onto each rack and uses a pneumatic device to load or unload a rack by a movement from the bottom upwards.

In such loading devices, it is not possible to ensure the agitation of the tubes.

The movement of the racks in an automatic analyzer is generally done linearly, the tubes being substantially vertical and their stopper being at the top. The rack therein is generally guided by rails. In such movement devices, it is not possible to ensure the agitation of the tubes. The document U.S. Pat. No. 4,609,017 describes a movement device using a conveyor belt which also serves as an agitation device. This solution does not allow perfect homogenization. The device is expensive and remains of limited reliability.

For the agitation, apart from the conveyor belt, other devices are described in the documents U.S. Pat. No. 4,921,676, FR2692358, FR2730315, FR2812088, U.S. Pat. No. 4,518,264. They make it possible to agitate one or more tubes removed from a rack, or a rack containing tubes. These devices are expensive and complex. Indeed, they require a mechanism dedicated to agitating the rack or the tubes in the movement device, and a mechanism for withdrawing them, before agitation, then returning them, after agitation.

Once the necessary sampling operations have been carried out in the tubes of a rack, the rack is arranged in a receptacle provided for this purpose. Such devices are described in the documents FR2692358 and FR2812088. The document U.S. Pat. No. 4,609,017 describes a vertical ejection system moved by a pneumatic device.

SUMMARY OF THE INVENTION

The purpose of the invention is to propose at least one simplified, reliable and effective device among devices allowing the handling of racks in an automated analysis apparatus. Moreover, such a device can preferably be used in an automated apparatus suitable for use in small laboratories.

Another purpose of the invention is to propose at least one method for handling racks, suitable for use by a device according to the invention.

Yet another purpose of the invention is to propose an apparatus, in particular an automated blood analysis apparatus, comprising a device according to the invention and/or implementing a method according to the invention.

According to a first objective of the invention, such an apparatus comprises a device for moving at least one rack in said apparatus, said rack forming a support for tubes, an apparatus further comprising means for taking a specimen of a product contained in said tubes, said movement device comprising means for guiding the rack during movement of said rack and further comprising means for agitating the guiding means, said movement device being mounted on a chassis of said apparatus. This apparatus is particularly suitable for being an automated product analyzer, in particular an automated blood analyzer.

Advantageously, the guidance means are means for holding the rack in the apparatus, such that during agitation, the rack is correctly held in the apparatus. The guidance means can be a rail cooperating with a complementary shape of the rack. This rail can have a C-shaped cross-section, two opposite ends of which extend towards each other and each forming a rib, said ribs being provided to engage with respective grooves on either side of a rack. Such an arrangement allows the rack to be held at the same time as it is guided, by the cooperation of the ribs and the complementary shapes, for example grooves, in the rack.

The movement device can comprise worm means for cooperating with a complementary shape of the rack, for example a nut, preferably partial. A stepping travel motor can be provided for driving the worm means in rotation. Thus, it is possible to know at any moment the position of a rack in the apparatus, which guarantees, in an analyzer, certain knowledge of the contents of whichever tube is being analyzed.

Preferably, the movement motor is mounted rigidly connected to the guidance means. Thus, the agitation of the rack does not cause a relative rotation of the worm or worms with respect to the guidance means, there is therefore a movement of the rack along the guidance means, for example along the rail.

The agitation means are preferably designed to allow a rotation of the rack about an axis parallel to a direction for the movement of the rack, for example in order to allow the rocking of the tubes between a position directed downwards close to the vertical, and a position, directed upwards, close to the vertical, such agitation making it possible to reproduce, with similar efficiency, the agitation which can be done manually by an operator.

For complete automation, an apparatus according to the invention advantageously comprises a loading device and/or an unloading device for the rack, said devices being advantageously fixed onto the chassis of the device.

The loading device can comprise a storage element for stacking several racks therein. The storage element can be designed to allow the movement under gravity of a rack in the storage element. Within the framework of a "first in/first out" type of operation, the loading device can comprise means for removing the lowest rack from the stack in the storage element.

The removal means can comprise a worm provided for engaging with a complementary shape of the rack, for example a nut-type shape, and a loading motor, preferably of the stepping type, for driving the worm.

The worm advantageously comprises a truncated zone in which the worm threads are interrupted beyond a plan parallel to the axis of rotation of said worm, said truncated zone being provided in order to allow a rack to adopt a position such that the worm, after rotation about said axis, can engage with said rack.

An unloading device for an apparatus according to the invention advantageously comprises a receptacle for unloaded racks. The movement device can be provided to move a rack right into a zone for receiving the receptacle.

The receptacle advantageously extends, for example on one side of the apparatus, following a substantially horizontal direction and substantially perpendicular to an axis of movement for a rack, in the movement device, and in that it further comprises means for displacing each rack a distance at least equal to the thickness of said rack, in the direction of extension of the receptacle. These displacement means can comprise one or more cams moved by a stepping motor.

A system, in particular a blood analysis system comprising an apparatus according to the invention and equipped with worm means for moving the rack, advantageously includes a rack comprising recesses together forming a portion of a nut for cooperating with the worm means. Such a rack can moreover be of the closed type, i.e. having a sampling wall opposite stoppers in the tubes, said sampling wall being pierced with openings allowing the penetration of a sampling needle.

According to a second objective of the invention, a method for handling a tube in an apparatus, said method comprises:
 the arrangement of the tube in a rack provided to serve as a support for said tube;
 the use of guidance means for guiding and holding the tube in the apparatus; and,
 rocking the guidance means.

Such a method is advantageously used to allow the movement of the tube and the homogenization of a blood product contained in the tube, with a view to the analysis of this blood product.

Other features and advantages of the invention will also become apparent from the description below, which relates to non-limitative examples.

BRIEF DESCRIPTION OF THE DRAWINGS

In the attached drawings.

DETAILED DESCRIPTION OF THE PREFERRED EMBODIMENTS

Figure 1:
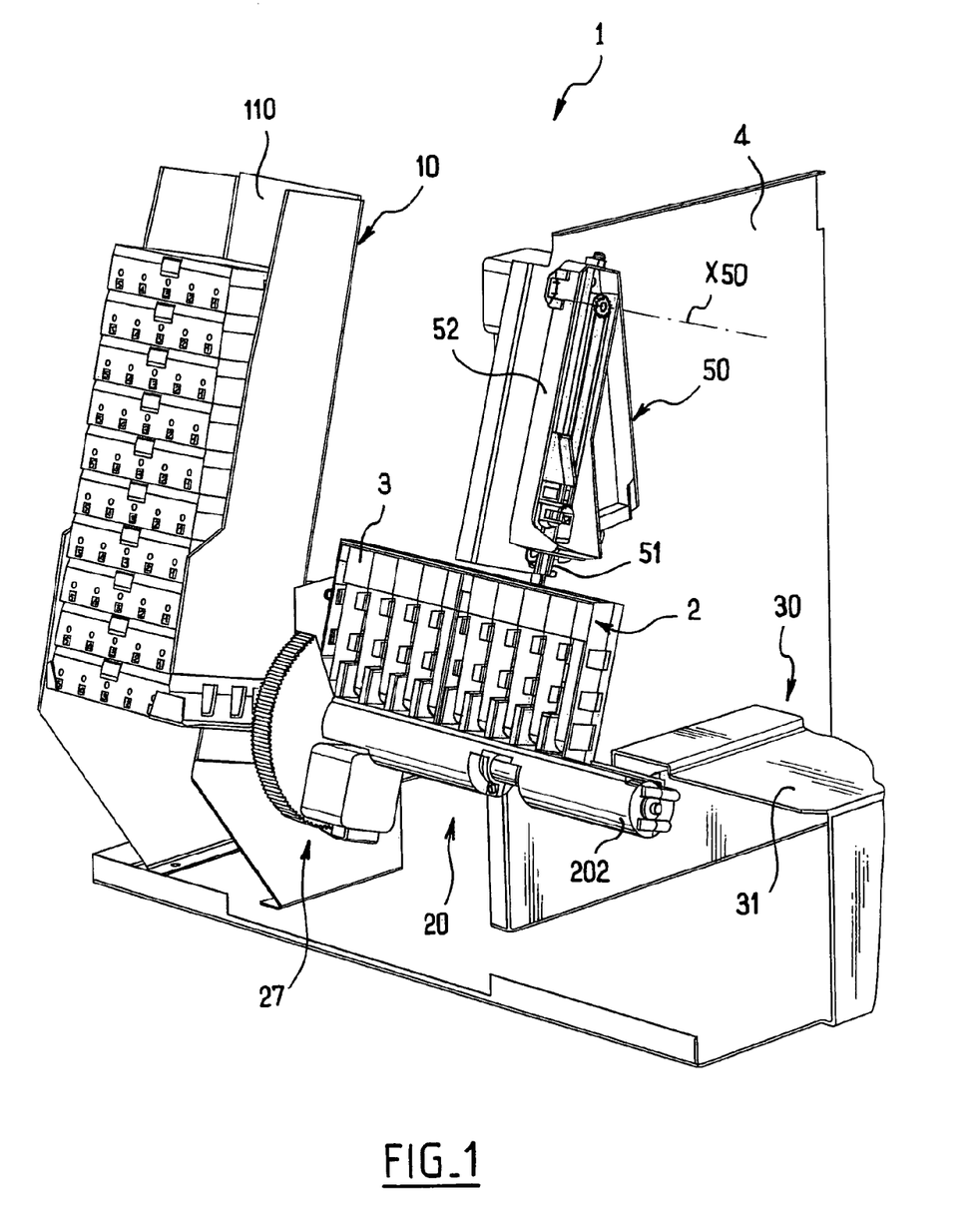
FIG. 1 is a three-quarter front perspective view of an automatic analyzer according to the invention.

FIG. 1 represents an automated blood analyzer 1 according to the invention. This automatic analyzer allows the handling of racks 2. As particularly illustrated in FIG. 8, each rack 2 is provided to contain five tubes 3, each containing a product, in this case a blood product, to be analyzed. The automatic analyzer 1 comprises a loading device 10, a movement and agitation device 20 and an unloading device 30 for the racks 2. The unloading device is only partially represented in order to simplify FIG. 1. The movement device 20 is provided to allow the movement of a rack from a loading position to an unloading position, by passing through an intermediate sampling position for a blood specimen in one of the tubes. The movement device further comprises agitation means 27, provided to allow the agitation of the tubes with a view to the homogenization of their content before sampling.

The automatic analyzer 1 further comprises a sampling device 50, in particular a needle 51, for the sample, partially represented in FIG. 1, and means of analysis, not shown, for the specimen taken.

The automatic analyzer 1 further comprises a chassis 4 bearing in particular all of the devices and means 10,20,30, 27,50 mentioned above as well as the analysis means.

Figure 7:
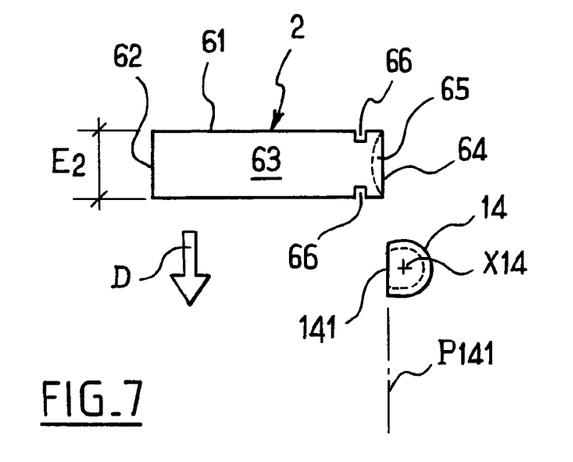
FIG. 7 is a diagrammatic illustration of the loading of the rack of
FIG. 6 into the automatic analyzer of FIG. 1.
Figure 8:
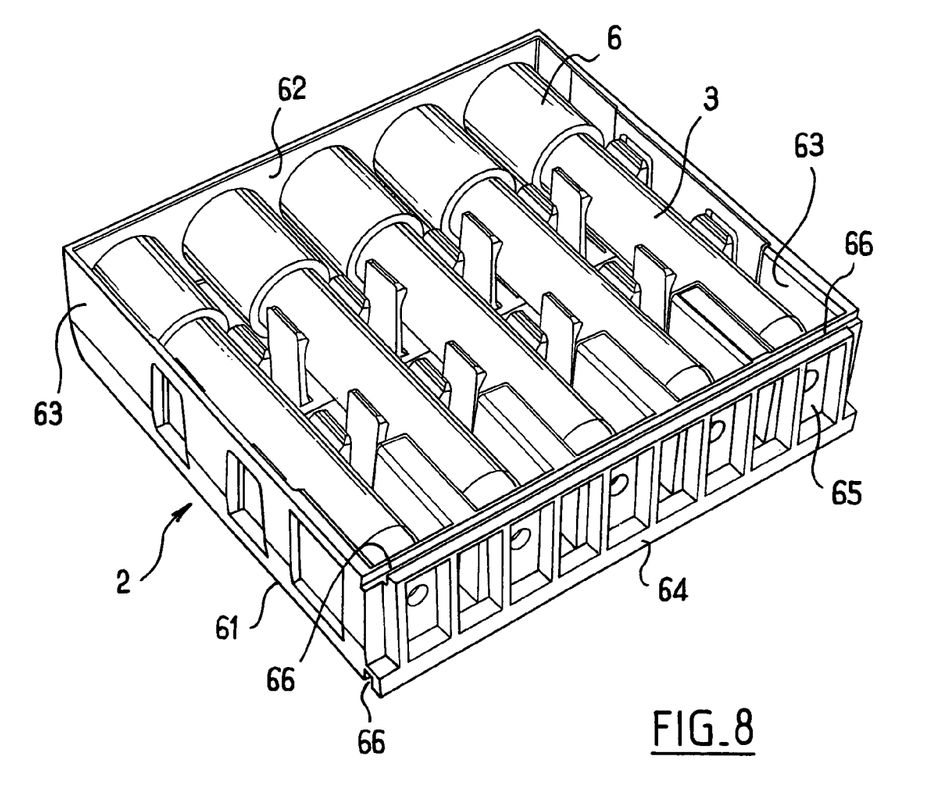
FIG. 8 is a perspective view of a rack suitable for use in the automatic analyzer of FIG. 1.

A rack 2 which can be used in the automatic analyzer of FIG. 1, is now more particularly described with reference to FIGS. 7 and 8. The rack 2 illustrated is in the form of a box. This box comprises a back 61 and four side walls 62,63,64 around, and perpendicular to, the back 61. The rack 2 illustrated is envisaged to contain up to five tubes 3; it is here shown full. The tubes 3 are detachably snapped onto the back and parallel to it. The rack 2 is completely open opposite the back 61, such that the tubes can be easily introduced into the rack or removed from it. The side walls extend from the back over a substantially constant distance, constituting a thickness E2 for each rack. In the example illustrated in the figures, the racks are provided identical to each other.

Among the side walls, a sampling wall 62 is arranged facing the stoppers 6 of the tubes 3. The sampling wall 62 is pierced through with sampling openings 67 (see particularly FIGS. 2, 4 and 6). Each opening 67 being arranged to be opposite a stopper 6 of a tube 3 in the rack 2, such that the sampling needle 51 can be introduced through the opening 67 then through a respective stopper 6 to take a sample from a given tube, as illustrated in FIG. 1.

Figure 9:
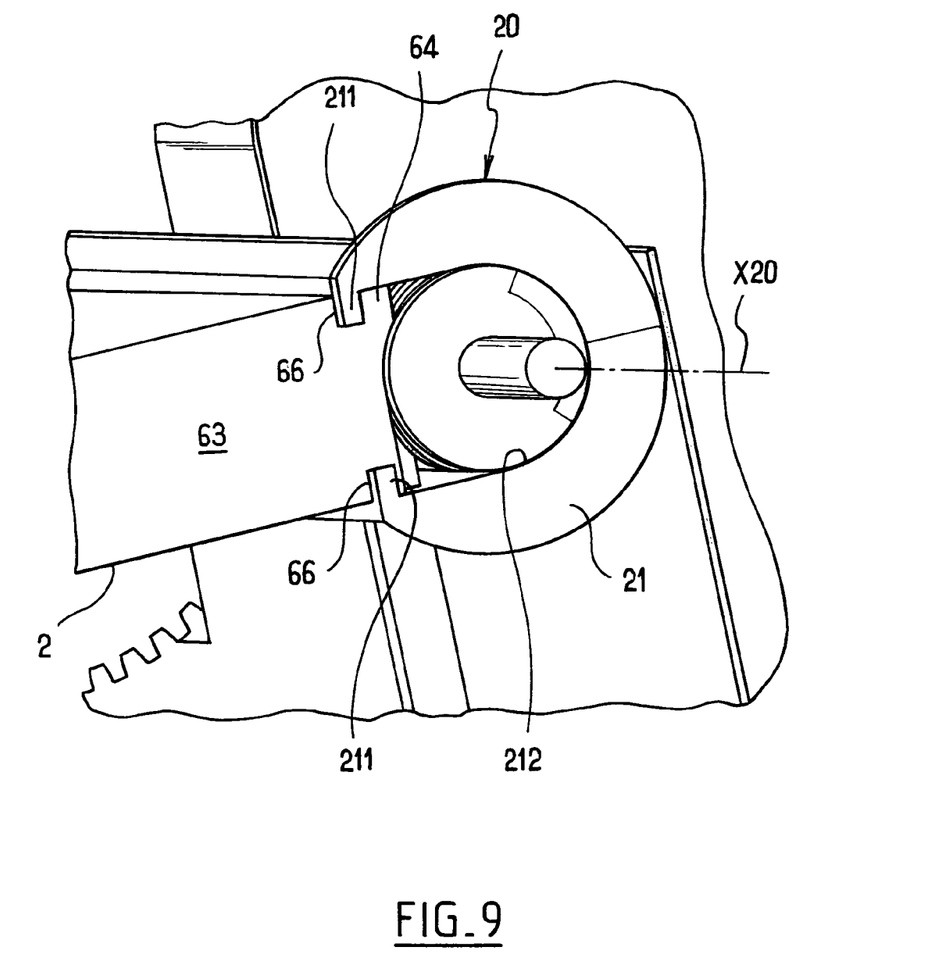
FIG. 9 is a diagrammatic illustration of the guiding and holding of the rack of FIG. 8 in the automatic analyzer of FIG. 1.

Another side wall 64, opposite the sampling wall 62, forms a basis 64 for the rack. The external surface of the basis 64 comprises recesses 65 extending from the back 61, transversally to the projection, such that the recesses 65 together form part of a nut, capable of engaging with a worm, for the movement of the rack in the automatic analyzer. The rack 2 further comprises, on either side of the basis 64, slots 66 in the side walls 63, slots parallel to the basis 64 and provided to engage with a guide rail 21, for guiding in translation the rack in the automatic analyzer (see in particular FIG. 9).

Figures 2, 3:
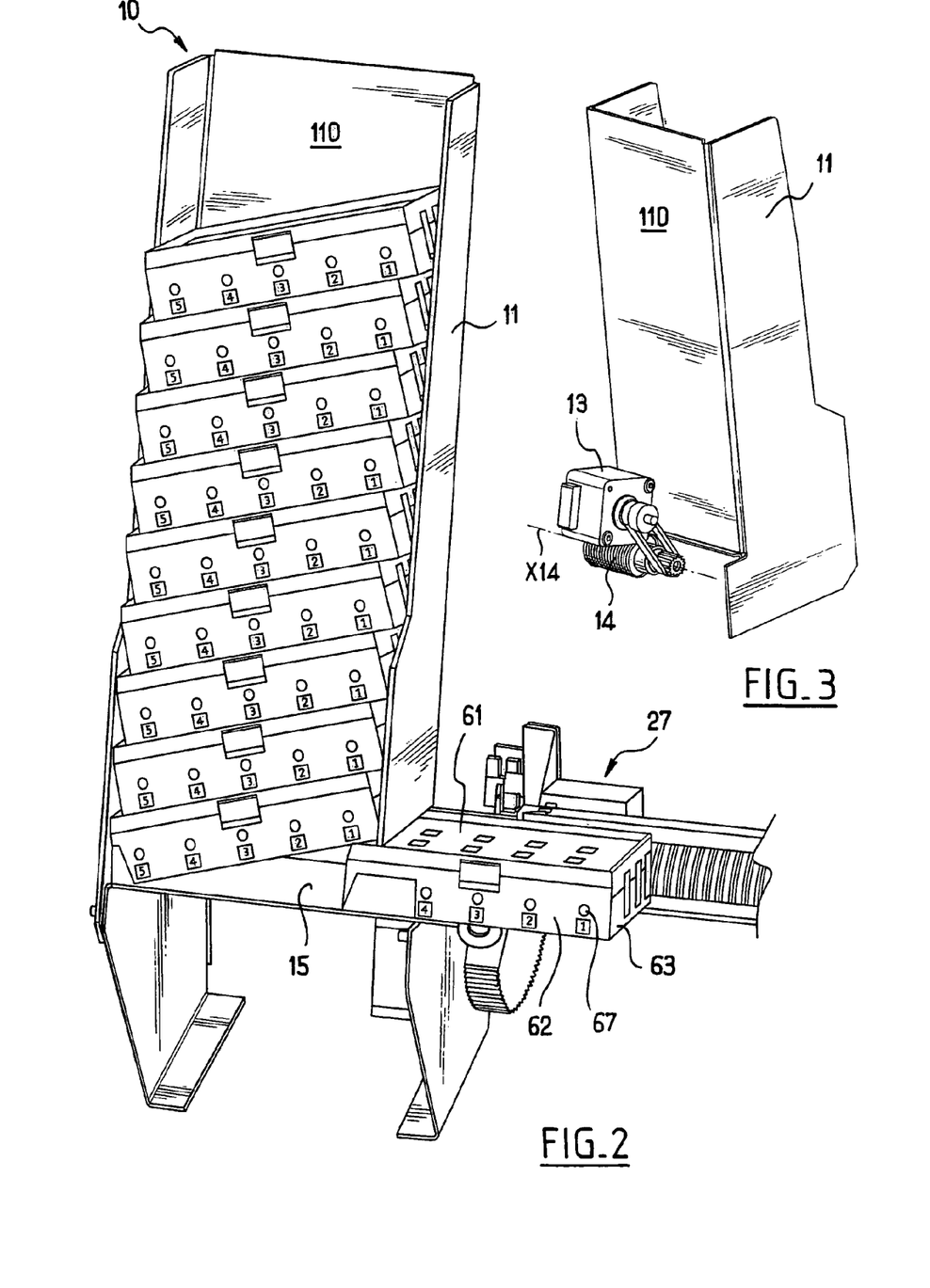
FIG. 2 is a general and a three-quarter front perspective view of a loading device of the automatic analyzer of FIG. 1.
FIG. 3 is a general and a rear three-quarter perspective view, on a reduced scale, of the loading of the automatic analyzer of FIG. 2.

The loading device 10 will now be described more particularly with reference to FIG. 2. In the example illustrated, the loading device comprises a storage element 11, provided to allow the substantially vertical stacking of several racks 2 stacked on top of each other, in a loading position.

The storage element 11 is slightly inclined towards the rear. Thus, a rear wall 110 of the loading device 11 forms a ramp 110 inclined such that the basis 64 of each rack 2 remains supported against the ramp, which allows correct positioning of the projection, the movement of the rack in the storage element being achieved by gravity.

In the loading position, the back 61 is above the tubes and the sampling wall 62 is oriented towards the front of the automatic analyzer. The loading device operates according to the principle "first in/first out", i.e. it is the rack underneath the stack, in a so-called bottom position, which is removed from the loading device in order to analyze its contents. The movement of any racks 2 not yet removed is achieved by gravity, until the bottom position is reached. FIG. 2 represents a rack in the process of being removed, the other racks contained in the storage element progressively taking up their new position in the storage device.

Means 13, 14 for removing the racks from the storage device 11 will now be described. The removal means comprise a loading motor 13 and a loading worm 14, with a horizontal axis X14. The worm 14 is envisaged to be driven by the motor 13. The motor is a stepping motor.

The worm 14 is arranged at the rear of the storage element, such that it can engage with the recesses 65 (see FIG. 8) of a rack when the latter is in the bottom position. As illustrated in FIG. 7, the worm 14 comprises a truncated zone 141. In the truncation zone 141, beyond a plane P141 parallel to its axis of rotation X14, the threads of the worm are interrupted. Thus, in a position as illustrated in FIG. 7, in order to allow the descent in the direction of D of a rack 2 into the bottom position in the storage element, the truncation zone is arranged towards the front relative to the axis X14. This arrangement allows a rack to take up the bottom position without being obstructed by the presence of the worm 14. When the rack has taken up the bottom position, the rotation of the worm 14 by the motor 13, allows the removal of the rack in order to introduce it into the movement and rocking device 20. The pitch of the worm 14 is oriented such that the rack in process of being removed is pushed downwards onto a plate 15, which forms a base for the storage element 11. The plate 15 serves as a reference for positioning relative to the movement device 20.

Figure 4:
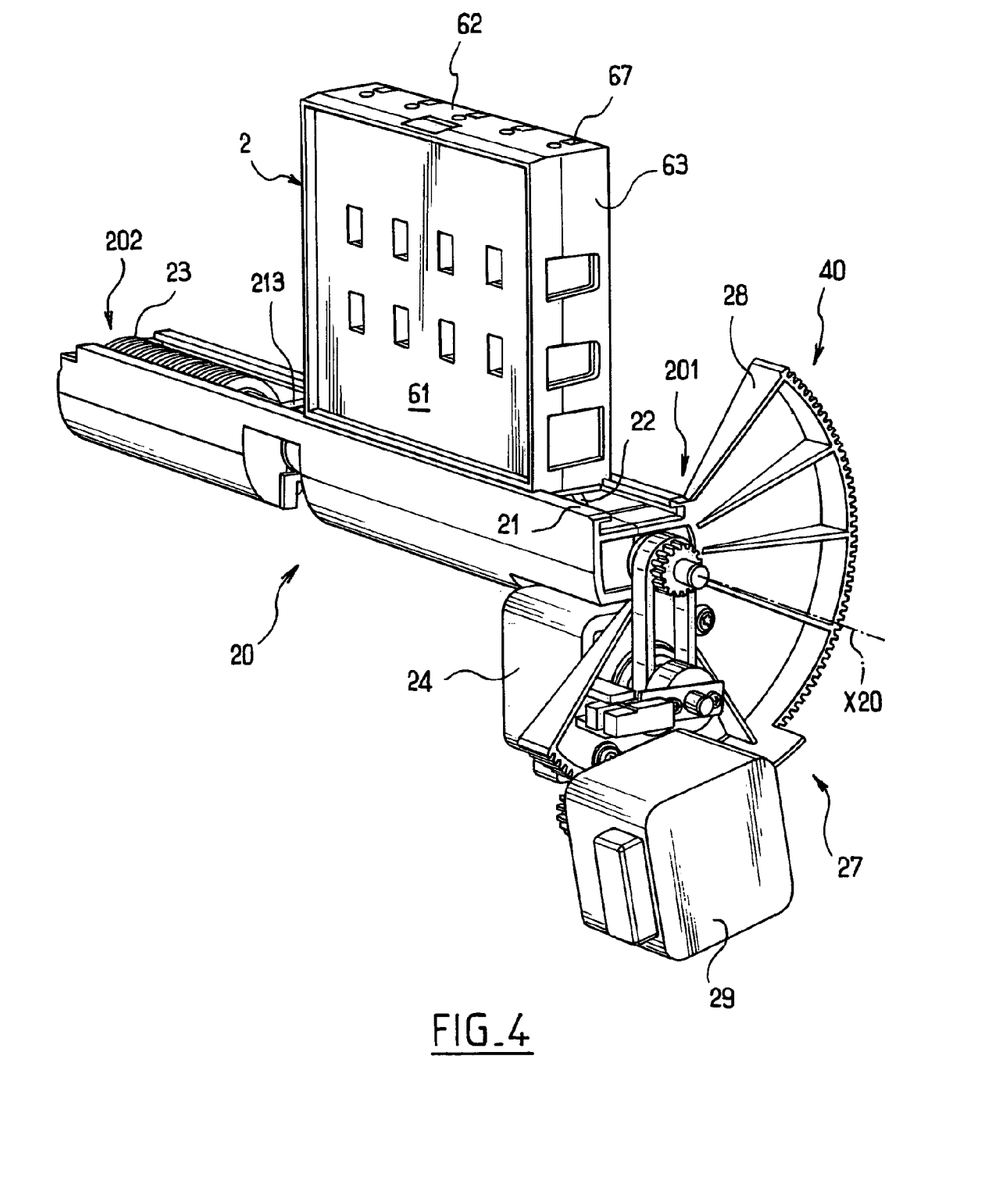
FIG. 4 is a rear three-quarter perspective view of a translation and agitation device of the automatic analyzer of FIG. 1.
Figures 5, 6:
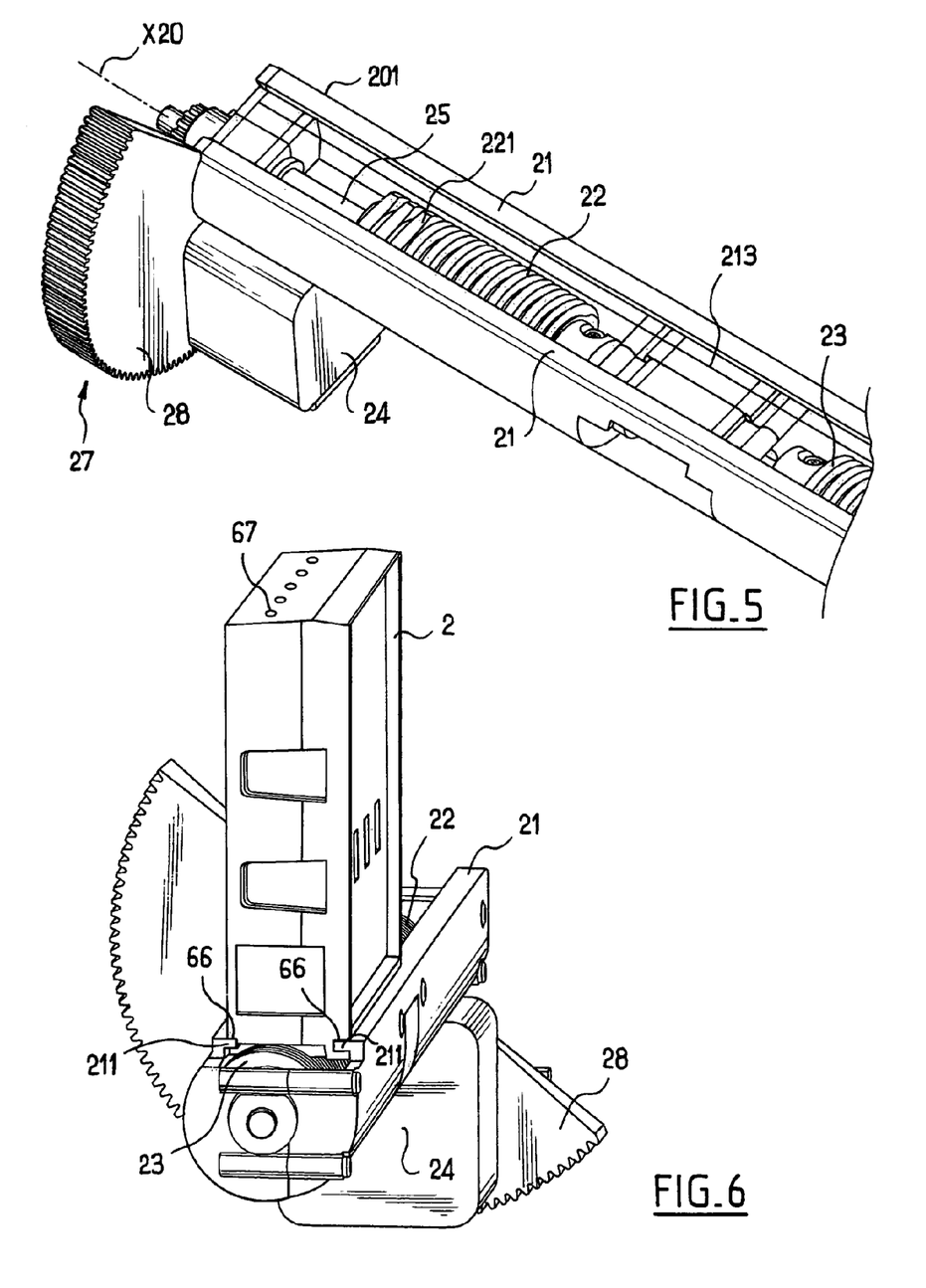
FIG. 5 is a perspective view from the front and from above of the translation and agitation device of the automatic analyzer of FIG. 4.
FIG. 6 is a profile and perspective view of the translation and agitation device of the automatic analyzer of FIG. 4.

The movement device 20 is in particular shown isolated from the rest of the automatic analyzer 1, in FIGS. 4-6. The movement device 20 is structured about an axis of movement X20 which merges with the loading axis X14. As illustrated in FIG. 1, it extends at the front of the automatic analyzer and transversally to the automatic analyzer, between a proximal end 201, adjacent to the loading device 10, and a distal end 202, adjacent to the unloading device 30.

The movement device 20 comprises means for guiding in translation 21. As particularly illustrated in FIG. 9, the guidance means form a rail 21 having a substantially C-shaped section transversal to and around the axis X20. Ends of the C extend towards each other and each form a rib 211. The ribs are provided to engage in the grooves 66 of a rack 2, each of the ribs 211 on a respective side of the projection 64 of the rack 2. The rail 21 comprises an internal surface 212 forming a portion of a cylinder coaxial with the axis X20. In order to allow the mounting of the movement device, by way of example, in the example illustrated, the rail is formed in two symmetrical parts along a plane containing the axis of movement X20.

The movement device 20 further comprises means of movement by worms 22, 23, 24 for driving the rack in transversal movement along the rail 21. These worm means comprise several worms 22, 23, mounted on a drive shaft 25, coaxial with the axis X20. A first 22 of the worms is arranged in the immediate vicinity of the proximal end 201; a second 23 is arranged in the immediate vicinity of the distal end 202.

The worms 22, 23 are mounted in rotation within the internal face 212 of the rail 21. The shaft 25 is borne by bearings 213 formed in two parts, each of a single piece with a respective part of the rail. The shaft 25, and the worms that it bears, are driven in rotation by a travel motor 24. The travel motor is mounted fixed relative to the rail 21. The travel motor is advantageously a stepping motor.

The movement device 20 further comprises agitation means 27. The agitation means 27 comprise a gear pinion 28 driven by a motor 29. The gear pinion 28 is a toothed sector forming an angle greater than 180°. The toothed sector is centred on the axis of movement X20. It is mounted rigidly fixed to the rail 21, and, in the example illustrated, it is made of a single piece with at least one of the parts of the rail 21.

During the removal of a rack 2 from the storage element 11, the rail 21 is arranged such that the removed rack engages with the rail, i.e. the ribs 211 engage with the slots 66 of the rack 2. The worm 14 of the loading device 10 moves the rack during the process of removal until it engages with the rail. The first movement worm 22 comprises at its proximal end a truncation 221 similar to the truncation 141 of the worm 14. When the rack has advanced sufficiently on the rail, along the truncation 221 of the movement worm 22, the first movement worm 22 is rotated and engages with the projection 65 of the rack 2 which it drives along the truncation 141 of the worm 14 until it is completely removed from the storage element 11 then, continues along the rail 21.

Once completely removed and taken up by the movement device 20, the rack can be agitated to allow the homogenization of its contents. For the agitation, the agitation means 27 is used, i.e. the rail is caused to rotate about its axis X20, and thus the rack borne by the rail is caused to tilt. Thus, the rack which has been removed substantially horizontally from the loading element 11 can be tilted downwards, such that the tubes contained are positioned stopper downwards, or tilted upwards, i.e. that the tubes are positioned stopper upwards. Thus, by an alternating downward and upward movement, it is possible to agitate the tubes with a movement similar to that which can be produced manually by an operator. This movement is therefore particularly effective. The ribs 211 of the guidance means, in engagement with the grooves 66 of the rack 2, ensure the rack is held in the movement device 20, therefore in the automatic analyzer, during its movement or of its agitation, whatever the position of the rack about the axis of movement X20.

The combined use of the means of movement by worm and means of rocking also makes it possible to bring the rack into a high position, tilted slightly towards the rear, as illustrated in FIG. 1, a position in which the sampling needle 51 can penetrate the stopper 6 of a tube 3 arranged opposite the needle 51 in order to take a blood specimen from it.

In a preferred embodiment, it is possible to interrupt the automatic operations and bring the rail into a low position, not shown, which means that the rack or racks optionally borne by the rail are directed downwards. There is then free access to the needle and an operator can manually present a single tube in order to take a sample from it. The needle is mounted on a swinging arm 52 articulated about a horizontal axis X50, such that the needle can be tilted towards the front in order to facilitate sampling from the isolated tube.

The rail is long enough for several racks, two racks in the example illustrated, to be simultaneously engaged with the rail, whilst allowing it to tilt. During the introduction of a new rack, the previous rack can be brought towards the loading device, such that the newly removed rack fits close to the previous rack. Thus, the position of the following rack is perfectly known relative to that of the previous rack. Moreover, due to the fact that the movement motor is rigidly fixed to the rail, the rocking does not cause any rotation of the worm means 22, 23 relative to the rail 21 and each rack remains immobile in translation during the rocking. Moreover, the use of a stepping motor, in particular for the movement motor, makes it possible to move the racks 2 on the rail 21, knowing the position of each tube at any moment. Thus, the racks can be successively moved in the automatic analyzer, from the loading device 10, as far as the unloading device 30, without any risk of mistaking a tube.

In particular, it may be useful to carry out a new analysis on the contents of an already analyzed tube, for example in order to check a result, when said already analyzed tube is arranged in a rack preceding a rack being analyzed. The time necessary to obtain the results of an analysis is shorter than the time necessary for taking the specimens from the tubes contained in a single rack. Thus, as the previous rack is still on the rail, it is possible, by reversing the rotation of the movement worms 22, 23, to move back the previous rack for a new analysis. Thanks to the precision of positioning, the already analyzed tube will be analyzed once again with the certainty of not mistaking the tube.

After the analysis of the tubes contained in a rack, the rack can be removed from the automatic analyzer in order to be reused subsequently, with new tubes. An automatic analyzer according to the invention advantageously comprises an unloading device 30, as partially illustrated in FIG. 1, and two embodiments of which are illustrated in FIG. 10 and in FIGS. 11, 12 respectively.

A first embodiment of an unloading device 30 illustrated by FIG. 10 will be described first. The unloading device 30 comprises a receptacle 31 for receiving the racks already analyzed. In FIG. 1, only the receptacle 31 is represented. The receptacle 31 is arranged on the right of the automatic analyzer 1, in the vicinity of the distal end 202 of the movement device 20. It comprises a receiving zone 35, situated at the front of the receptacle 31, for receiving the racks immediately upon leaving the movement device 20. The receiving zone 35 is in the immediate vicinity and in alignment with the distal end 202. The receptacle 31 extends substantially horizontally, from the receiving zone 35 towards the rear of the automatic analyzer. The receptacle is provided for receiving the racks arranged vertically, the basis 64 oriented downwards and the backs 61 of the racks being orientated towards the rear, such that the thickness E2 of the racks extends horizontally, from the front to the rear.

Figure 10:
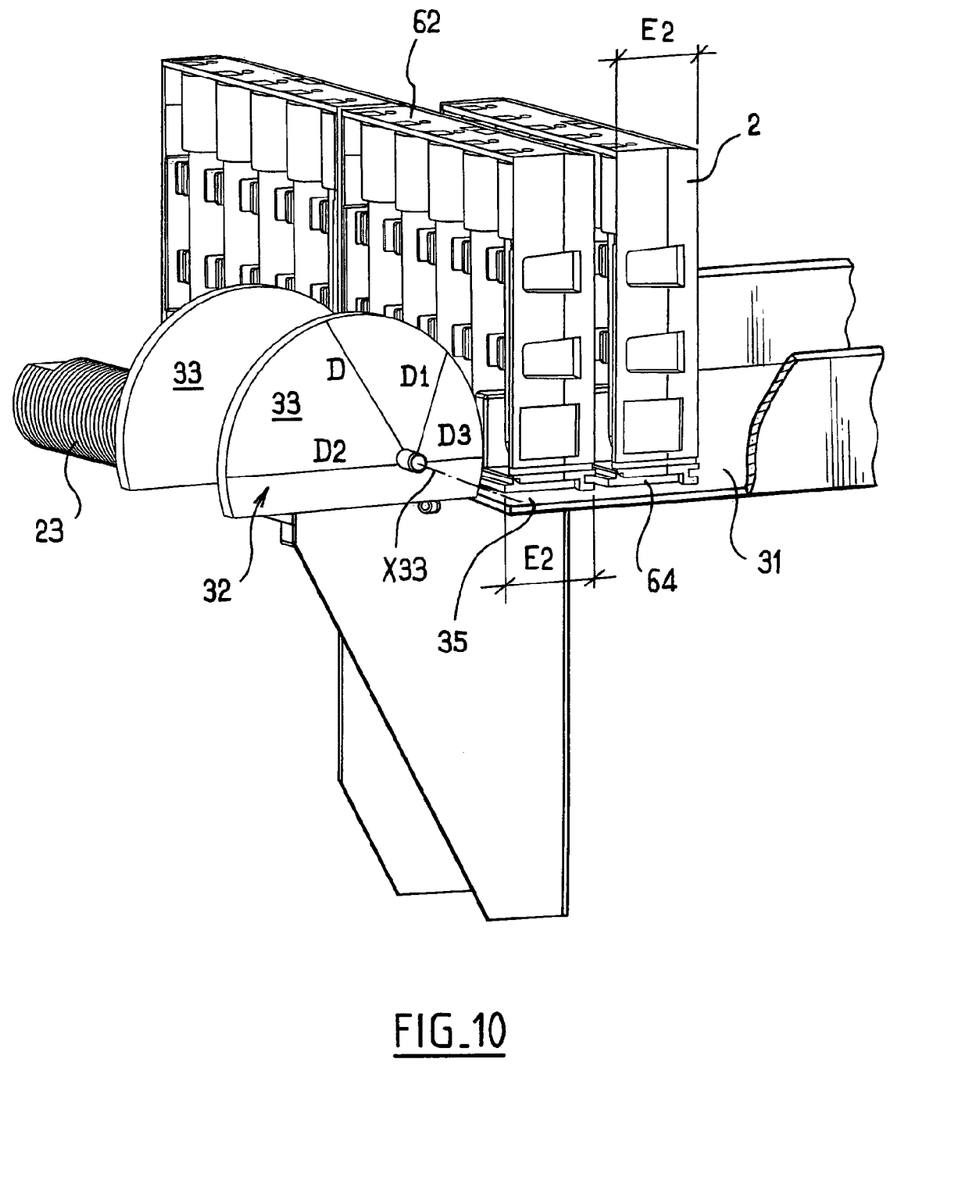
FIG. 10 is a perspective view of a first embodiment of an unloading device for the automatic analyzer of FIG. 1; and,
FIGS. 11 and 12 are two perspective views of a second embodiment of an unloading device for the automatic analyzer of FIG. 1.

In the embodiment particularly illustrated in FIG. 10, the unloading device 30 further comprises displacement means 32, for the successive displacement of the racks unloaded from the receiving zone towards the rear of the receptacle 31. The displacement means 32 comprise two cams 33. The two cams are mounted in rotation about a horizontal cam axis X33. The cam axis 33 is substantially parallel to the axis of movement X20. The cams are moved in rotation about the cam axis X33 by a stepping motor, not shown in FIG. 10. The cams 33 are provided to be supported simultaneously, each against a respective side wall 63 of a rack in the receiving zone 35. The, cams are identical to each other. Each cam is in the form of an disc which is off-centre relative to the cam axis X33, such that the distance D to the axis X33 varies at least between a short distance to the axis D1 and a long distance to the axis D2, the difference D2-D1 being equal to the thickness E2 of a rack 2.

The unloading of a rack from the movement device 20 is carried out when the rack to be unloaded is tilted vertically upwards, i.e. when the sampling wall is oriented upwards. Moreover, in order for the receiving zone to be freely accessible, the cams must, prior to the unloading, be arranged such that they have, opposite the receiving zone 35, a distance D3 to the axis X33 less than or equal to the short distance D1. By the action of the second movement worm 23 on its basis 64, the rack to be unloaded is brought into the receiving zone 35. Then, the cams are rotated such that the distance D to the axis X33, opposite the receiving zone 35 progressively increases. When the distance reaches D1, the cams come into contact with the rack and begin to displace it towards the rear of the receptacle 31, until the distance D reaches or exceeds the distance Dl. The receiving zone is then cleared once again, ready for the unloading of a new rack. Each rack displaced by the displacement device is supported on any previously displaced rack, progressively forming a line of unloaded racks. The receptacle 31 is advantageously designed in order to be able to receive a number of racks at least equal to the number of racks provided to be stored in the storage element 11.

A second preferred embodiment of an unloading device 30 illustrated by FIGS. 11 and 12 will now be described, essentially to the extent that it differs from the embodiment illustrated in FIG. 10. In this second embodiment, the receiving zones 35 and the receptacle 31 are similar to those previously described. By contrast, the displacement system 70 used here is a pallet system 70. The displacement system 70 comprises a pallet 71 formed from a single piece with a casing 72. The casing and the pallet are formed and arranged such that the pallet extends substantially from the casing, upwards, above the receiving zone 35, and the casing 72 extends downwards, from the pallet, below the receiving zone 35. The casing is freely articulated about a pallet axis X70. The pallet axis X70 is substantially parallel to the axis X20. The axis X70 is arranged through the bottom part of the casing.

Figures 11, 12:
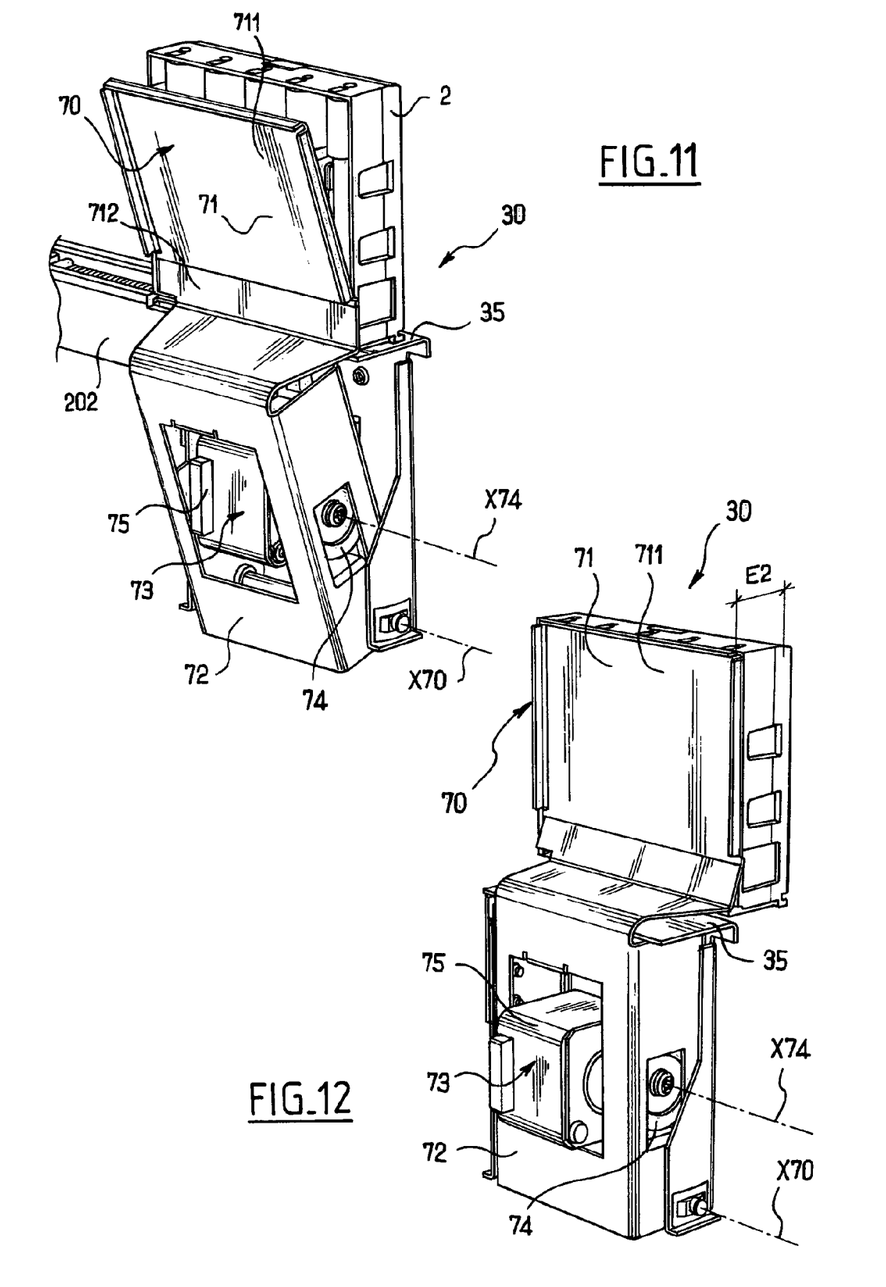

FIG. 11 illustrates a standby position for the thrust system 70. FIG. 12 illustrates a thrust position for the thrust system. The thrust system is mounted mobile in rotation about the axis X70, between the waiting position and the thrust position. The movement of the thrust system between the two positions is ensured by tilting means 73. These tilting means comprise an eccentric 74 mounted in rotation about an axis of the eccentric X74, parallel to the pallet axis X70. The eccentric is driven in rotation by a motor 75. It is mounted inside the casing 72, between two opposite walls of said casing, such that its rotation, supported on the opposite walls, causes the tilting of the casing, and therefore of the pallet 71.

The pallet has a connecting zone 712 with the casing 72, formed such that, in the standby position, the connecting zone 712 forms a flat and vertical wall which serves as a guide, at the front of the receiving zone 35, for a rack 2 introduced by the movement means 20 into the receiving zone 35. In the standby position, a thrust zone 711 of the pallet 71 forms a flat wall extending from the connecting zone upwards and forwards from the connecting zone 712. The thrust zone 711 is formed such that in the thrust position, the thrust zone is vertical, and arranged beyond the receiving zone rearwards.

Thus, when a rack is introduced into the receiving zone 35, it is first guided by the connecting zone 712. Then, when the rack is completely in the receiving zone, i.e. in particular it is no longer engaged with the guidance device 20, the rocking of the pallet towards the rear as far as the thrust position makes it possible to bring the rack onto the receptacle 31, by pushing any racks previously unloaded and simultaneously freeing the receiving zone 35.

Of course, the invention is not limited to the examples which have just been described, and numerous adjustments can be made to these examples without exceeding the scope of the invention.

In particular, the automatic analyzer can be envisaged to be used with other types of rack, in particular racks provided in order to contain a number of different tubes, or open racks, i.e. with no wall opposite the stoppers.

Instead of a loading of the racks by gravity, mechanical loading can be provided, for example horizontal, for example with thrust means similar to the unloading means, or by the action of a spring.

The agitation can also be provided by any rotation, possibly even up to 360°. It is however preferable to ensure at least one 180° rocking movement, between a position close to the vertical upwards and a position close to the vertical downwards.

The idea of the rail must be understood in the broad sense. For example, the function of the rail can be ensured by at least partially magnetic guidance and holding means.

The invention claimed is:

1. An apparatus (1), comprising:
   a movement device (20) for moving at least one rack (2) containing tubes (3); and
   means (50) for taking a specimen of a product contained in said tubes (3), said movement device (20) comprising:
   guide rails (21) configured to guide the rack (2) during a movement of said rack along an axis of movement, said guide rails configured to engage with slots (66) in side walls (63) of the rack (2) parallel to a basis (64) of the rack at any position of the rack along said axis of movement,
   worm means (22, 23) configured to cooperate with a complementary structure of the rack (2), an external surface of the basis (64) of the rack (2) comprising recesses (65) extending from a back (61) of the rack transversally to the external surface of the basis (64), the recesses (65) engaging directly with the worm means (22, 23) such that an operational rotation of said worm means causes a translation of the rack along said axis of movement, a first rotation of the worm means in a first direction causing the rack to translate in a first direction along the axis of movement, and a second rotation of the worm means in an opposite second direction causing the rack to translate in an opposite second direction along the axis of movement, and
   an agitating mechanism (27) configured to agitate said guide rails, said agitating mechanism comprising a gear pinion (28) rigidly affixed to the guide rails (21), and an agitation motor configured to drive the gear pinion (28), said agitating mechanism configured to drive a rotation of the rack about an axis that is parallel to the axis of movement.

2. The apparatus according to claim 1, wherein said apparatus is an automatic analyzer for the product.

3. The apparatus according to claim 1, wherein the guide rails comprise a rail (21) that cooperates with a complementary shape (66) of the rack.

4. The apparatus according to claim 3, wherein the rail has a C-shaped cross-section, two opposite ends of which extend towards each other, and each forming a rib (211), said ribs being provided to engage with respective grooves (66) on either side of the rack.

5. The apparatus according to claim 4, wherein the worm means are arranged inside the C-shaped section.

6. The apparatus according to claim 1, further comprising:
   a stepping travel motor (24) that drives the worm means (22, 23) in rotation.

7. The apparatus according to claim 6, wherein the travel motor (24) is rigidly mounted to the guide rails.

8. The apparatus according to claim 1, wherein the agitation motor is a stepping agitation motor.

9. The apparatus according to claim 1, wherein the agitating mechanism operationally rocks the tubes between a position directed downwards and a position directed upwards.

10. The apparatus according to claim 1, further comprising:
    a loading device (10).

11. The apparatus according to claim 10, wherein the loading device comprises a storage element (11) sufficient such that a plurality of racks (2) can be stacked therein.

12. The apparatus according to claim 11, wherein the storage element is capable of movement by gravity of each rack in the storage element.

13. The apparatus according to claim 11, further comprising:
    removal means (13, 14) for removing the lowest rack from a stack of racks in the storage element.

14. The apparatus according to claim 13, wherein the removal means comprise a removing worm (14) engageable with the recesses of the rack.

15. The apparatus according to claim 14, further comprising:
    a stepping loading motor (13) for driving the removing worm.

16. The apparatus according to claim 14,
    wherein the removing worm includes a truncated zone (141) in which threads of the removing worm end at a plane (P141) parallel to an axis of rotation (X14) of said removing worm, and
    wherein said truncated zone permits a rack to be removed to take up a position such that the removing worm, after rotation about said axis (X14), engages with said rack.

17. The apparatus according to claim 1, further comprising:
    an unloading device (30).

18. The apparatus according to claim 17, wherein the unloading device comprises a receptacle (31) for unloaded racks.

19. The apparatus according to claim 18, wherein the movement device (20) is provided to move a rack into a receiving zone (35) of the unloading device (30).

20. The apparatus according to claim 19,
    wherein the receptacle (31) extends in a substantially horizontal direction and substantially perpendicular to an axis of movement for a rack in the movement device, and
    wherein the apparatus further comprises displacement means (32, 70) for displacing each rack for a distance at least equal to a thickness (E2) of said each rack in a direction of extension of the receptacle (31).

21. The apparatus according to claim 20, wherein the displacement means comprise a cam (33) or a pallet (71) moved via a stepping motor.

\* \* \* \* \*